United States Patent [19]
Frisbee et al.

[11] Patent Number: 5,213,811
[45] Date of Patent: May 25, 1993

[54] ORAL SUSTAINED-RELEASE DRUG COMPOSITIONS

[75] Inventors: Steven E. Frisbee, Austin, Tex.; Gregg Stetsko, Bethlehem; Margaret A. Lawton, Albany, both of N.Y.

[73] Assignee: Sterling Drug Inc., New York, N.Y.

[21] Appl. No.: 759,347

[22] Filed: Sep. 13, 1991

[51] Int. Cl.$^5$ .................................. A61K 9/54
[52] U.S. Cl. ........................ 424/493; 424/451; 424/456; 424/457; 424/458; 424/459; 424/461; 424/462; 424/489; 424/494; 424/495; 424/497; 424/499; 514/962; 514/963; 514/964
[58] Field of Search .............. 424/451, 457, 458, 459, 424/461, 462, 489, 494, 495, 499, 456, 493, 497; 514/962, 963, 964

[56] References Cited

U.S. PATENT DOCUMENTS

| | | | |
|---|---|---|---|
| 2,738,303 | 3/1956 | Blythe | 424/458 |
| 2,921,883 | 1/1960 | Reese et al. | 424/458 |
| 4,540,602 | 9/1985 | Motoyama et al. | 424/495 X |
| 4,708,867 | 11/1987 | Hsiao | 424/462 X |
| 4,752,470 | 6/1988 | Mehta | 424/458 |
| 4,800,084 | 1/1989 | Zerbe | 424/458 |
| 4,806,361 | 2/1989 | Harrison et al. | 424/495 |
| 5,026,560 | 6/1991 | Makino et al. | 424/494 |

*Primary Examiner*—Thurman K. Page
*Assistant Examiner*—Robert H. Harrison
*Attorney, Agent, or Firm*—Theodore C. Miller; Paul E. Dupont; Imre Balogh

[57] ABSTRACT

Sugar or sugar/starch beads coated with a first coating of a drug, for example 1,2-dihydro-6-(lower alkyl)-2-oxo-5-(4-pyridinyl)-nicotinonitrile (milrinone), hydroxypropyl methylcellulose or hydroxypropyl cellulose and a plasticizer selected from triacetin, diacetylated monoglycerides, glycerin, propylene glycol, polyethylene glycol, diethyl phthalate and triethyl citrate or a mixture of two or more thereof and a second coating of high-viscosity ethylcellulose, low-viscosity ethylcellulose, hydroxypropyl cellulose, polyvinyl acetate phthalate and a plasticizer selected from diacetylated monoglycerides and triacetin or a mixture thereof and optionally coated with additional first coating and capsules filled therewith and method of preparation thereof are disclosed.

13 Claims, No Drawings

ORAL SUSTAINED-RELEASE DRUG COMPOSITIONS

BACKGROUND OF THE INVENTION

1. Field of the Invention

The invention relates to sustained-release coated-bead compositions containing a drug for oral administration, capsules filled therewith and method of preparation thereof wherein the drug is highly soluble in gastric fluid and much less soluble in intestinal fluid.

2. Information Disclosure Statement

Harrison et al. U.S. Pat. No. 4,806,361 issued Feb. 21, 1989 describes (column 3, lines 48–68)

... a sustained-release unit dosage form of a medicament of the 1,2-dihydro-3-cyano-6-lower-alkyl-5-(4-pyridinyl)-2(1H)-pyridinone class for oral administration comprising beads composed of an inert particulate core having adhered thereto a coating comprising said medicament, wherein each bead of said medicament-coated inert particulate core is surrounded by a sustaining coating comprising at least three admixed polymers, one of said polymers being soluble in gastric juices at all pH values normally encountered, a second of said polymers being insoluble in gastric juices at pH values below about 5 but soluble therein at pH values of about 5 and above and the third of said polymers being insoluble in the contents of the gastrointestinal tract at all pH values normally encountered, the portions as to permit a substantially uniform release of the medicament present notwithstanding the differing solubilities at the differing pH values prevailing during passage of the beads through the stomach and the gastrointestinal tract of a patient.

1,2-Dihydro-3-cyano-6-methyl-5-(4-pyridinyl)-2(1H)-pyridinone is the preferred 1,2-dihydro-3-cyano-6-lower-alkyl-5-(4-pyridinyl)-2(1H)-pyridinone. Hydroxypropylmethylcellulose is the preferred first polymer, which may also be polyvinylpyrrolidone or sodium carboxymethylcellulose. Hydroxypropylmethylcellulose phthalate is the preferred second polymer, which may also be a copolymer of the lower alkyl methacrylates. Ethylcellulose is the preferred third polymer, which may also be a copolymer of the lower alkyl methacrylates in which the copolymerising monomer contains a hydrophilic group. An adhesive, for example hydroxypropylmethylcellulose, is used to adhere the medicament to the particulate core.

The invention has the following advantages over the prior art including the compositions of Harrison et al. U.S. Pat. No. 4,806,361: 1) use of a toxic organic solvent, methylene chloride, is avoided; 2) the process of preparation is less sensitive to process variations; 3) the sustained release film has better mechanical strength; and 4) use of two portions of beads, one containing an immediate release dose and one containing a sustained release dose, is avoided.

SUMMARY OF THE INVENTION

In a first composition of master aspect the invention is sugar or sugar/starch beads coated with from about 1% to about 500% by weight of the beads of a first coating consisting essentially of from about 10% to about 90% by weight of a drug having a solubility of at least 5% by weight in gastric fluid and less than 1% by weight in intestinal fluid, from about 10% to about 20% by weight of hydroxypropyl methylcellulose or hydroxypropyl cellulose and from about 1% to about 10% by weight of a plasticizer selected from triacetin, diacetylated monoglycerides, glycerin, propylene glycol, polyethylene glycol, diethyl phthalate and triethyl citrate or a mixture of two or more thereof and from about 3% to about 50% by weight of the beads of a second coating consisting essentially of from about 30% to about 50% by weight of ethylcellulose having a viscosity from 40 to 60 centipoises, from about 10% to about 30% by weight of ethylcellulose having a viscosity from 1 to 20 centipoises, from about 10% to about 30% by weight of hydroxypropyl cellulose, from about 10% to about 30% by weight of polyvinyl acetate phthalate and from about 1% to about 20% by weight of a plasticizer selected from diacetylated monoglycerides and triacetin or a mixture thereof.

The first composition of matter aspect of the invention provides sustained release of the drug as the composition passes through the gastrointestinal tract.

In a second composition of matter aspect the invention is the first composition of matter aspect of the invention additionally coated with from about 1% to about 100% by weight of the beads of the first coating thereof.

The second composition of matter aspect of the invention provides initial rapid release of the drug and then sustained release of the drug as the composition passes through the gastrointestinal tract.

In a third composition of matter aspect the invention is a pharmaceutical capsule filled with from about 40 milligrams to about 700 milligrams of the first composition of matter aspect of the invention.

In a fourth composition of matter aspect the invention is a pharmaceutical capsule filled with from about 40 milligrams to about 700 milligrams of the second composition of matter aspect of the invention.

In a first process aspect the invention is the method of preparing the first composition of matter aspect of the invention which comprises dissolving the hydroxypropyl methylcellulose or hydroxypropyl cellulose and the plasticizer selected from triacetin, diacetylated monoglycerides, glycerin, propylene glycol, polyethylene glycol, diethyl phthalate and triethyl citrate or mixture of two or more thereof in water with or without warming, suspending the drug in the resulting solution, coating the beads with the resulting first coating suspension, dissolving the 40–60 centipoise ethylcellulose, the 1–20 centipoise ethylcellulose, the hydroxypropyl cellulose, the polyvinyl acetate phthalate and the plasticizer selected from diacetylated monoglycerides and triacetin or mixture thereof in a mixture of ethanol and water with or without warming, and coating the first-coated beads with the resulting second coating solution.

In a second process aspect the invention is the method of preparing the second composition of matter aspect of the invention which comprises carrying out the first process aspect of the invention and then coating the resulting coated beads with additional first coating suspension.

DETAILED DESCRIPTION OF THE INVENTION INCLUSIVE OF THE PREFERRED EMBODIMENTS

The drug can be any drug having a solubility of at least 5% by weight in gastric fluid and less than 1% by weight in intestinal fluid. Such a drug is generally characterized by a basic nitrogen functional group whereby solubility results from formation of an acid addition salt with the hydrochloric acid of gastric fluid and insolubility results from conversion of the hydrochloride salt to the free base and by lack of any functional group whereby solubility results from formation of a base addition salt under the alkaline condition of intestinal fluid. The 1,2-dihydro-6-(lower alkyl)-2-oxo-5-(4-pyridinyl)-nicotinonitriles described by Lesher et al. U.S. Pat. No. 4,313,951 issued Feb. 2, 1982, which are useful as cardiotonic agents and whose basic nitrogen functional group is 4-pyridinyl, are examples. 1,2-Dihydro-6-methyl-2-oxo-5-(4-pyridinyl)nicotinonitrile, which is described as the product of example B-1 thereof and whose generic name is milrinone (The Merck Index, Eleventh Edition, 1989, monograph 6117), is a specific example. The drug is preferably micronized to produce a smooth surface for the first coating. Micronization is carried out by conventional technique.

The other substances used to prepare the first composition of matter aspect of the invention are known pharmaceutical or food ingredients. The preferred plasticizer of the first coating is triacetin. The preferred plasticizer of the second coating is diacetylated monoglycerides. These and the other substances used to prepare the below-described example are described by The United States Pharmacopeia, Twenty-second Revision and The National Formulary, Seventeenth Edition (a single volume also entitled 1990 USP XXII NF XVII; copyright by United States Pharmacopeial Convention, Inc., 12601 Twinbrook Parkway, Rockville, Md. 20852, 1989). A set of monographs is presented and arranged alphabetically by name in each of the United States Pharmacopeia (USP) and National Formulary (NF) sections thereof. The convention followed thereby in naming the substances described is that the first letter of each word of the name is capitalized. The substances used to prepare the below-described example are described under the following names (section, page(s)): Hydroxypropyl Methylcellulose (USP, pp. 670–671), Triacetin (USP, p. 1392), Diacetylated Monoglycerides (NF, pp. 1925–1926), Ethylcellulose (NF, p. 1930), Hydroxypropyl Cellulose (NF, p. 1938), Polyvinyl Acetate Phthalate (NF, pp. 1968–1969), Sugar Spheres (NF, p. 1989). Other domestic and foreign pharmaceutical texts describe equivalent substances in similar terms.

Hydroxypropyl Methylcellulose is described as "[c]ellulose, 2-hydroxypropyl methyl ether" and as "a propylene glycol ether of methylcellulose", which "[w]hen dried at 105° C. for 2 hours . . . contains methoxy ($OCH_3$) and hydroxypropoxy ($OCH_2CHOHCH_3$) groups" conforming to certain limits. Hydroxypropyl Methylcellulose 2910 is the preferred hydroxypropyl methylcellulose of the invention and has a minimum of 28.0% and a maximum of 30.0% of methoxy groups and a minimum of 7.0% and a maximum of 12.0% of hydroxypropoxy groups. Specifications are set forth for three other variants, which are designated by the numbers 1828, 2208 and 2906. A procedure is described for determining viscosity and the following permitted viscosity limits are set forth:

Its viscosity is not less than 80.0% and not more than 120.0% of that stated on the label for viscosity types of 100 centipoises or less, and not less than 75.0% and not more than 140.0% of that stated on the label for viscosity types higher than 100 centipoises.

Hydroxypropyl Methylcellulose 2910 having a viscosity of 6 centipoises is preferred.

Triacetin is described as well by the names "1,2,3-[p]ropanetriol triacetate" and "[g]lycerin triacetate" and by the structural formula

and is specified as containing "not less than 97.0 percent and not more than 100.5 percent of $C_9H_{14}O_6$, calculated on the anhydrous basis."

Diacetylated Monoglycerides is described as

. . . glycerin esterified with edible fat-forming fatty acids and acetic acid. It may be prepared by the interesterification of edible oils with triacetin in the presence of catalytic agents, followed by molecular distillation, or by the direct acetylation of edible monoglycerides with acetic anhydride without the use of catalyst or molecular distillation.

Ethylcellulose is described as "an ethyl ether of cellulose" and by the statement that "[w]hen dried at 105° for 2 hours, it contains not less than 44.0 percent and not more than 51.0 percent of ethoxy ($-OC_2H_5$) groups." A procedure is described for determining viscosity and the following permitted viscosity limits are set forth:

The viscosity is not less than 90.0% and not more than 110.0% of that stated on the label for a labeled viscosity of 10 centipoises or more; not less than 80.0% and not more than 120.0% of that stated on the label for a labeled viscosity of less than 10 centipoises but more than 6 centipoises; and not less than 75.0% and not more than 140.0% of that stated on the label for a labeled viscosity of 6 centipoises or less.

The high-viscosity ethylcellulose of the invention preferably has a viscosity from 45 to 55 centipoises, most preferably about 50 centipoises. The low-viscosity ethylcellulose of the invention preferably has a viscosity from 15 to 25 centipoises, most preferably about 10 centipoises.

Hydroxypropyl Cellulose is described as "[c]ellulose, 2-hydroxypropyl ether" and as . . . a partially substituted poly(hydroxypropyl) ether of cellulose. It may contain not more than 0.60 percent of silica, or other suitable anticaking agents. When dried at 105° for 3 hours, it contains not more than 80.5 percent of hydroxypropoxy groups.

Polyvinyl Acetate Phthalate is described as

. . . a reaction product of phthalic anhydride and a partially hydrolyzed polyvinyl acetate. It contains not less than 55.0 percent and not more than 62.0 percent of phthalyl (o-carboxybenzoyl, $C_8H_5O_3$) groups, calculated on an anhydrous acid-free basis.

Sugar Spheres are described as containing "not less than 62.5 percent and not more than 91.5 percent of sucrose ($C_{12}H_{22}O_{11}$), calculated on the dried basis, the remainder consisting chiefly of starch" and as consisting of "approximately spherical particles of a labeled nominal size range" and correspond to the sugar or sugar/starch beads of the invention. They can also be or be referred to as granules, particles, pellets or nonpareils and are from about 2 millimeters or about 10 mesh to about 0.2 millimeter or about 80 mesh, preferably from about 15 mesh to about 40 mesh, in diameter or longest dimension before coating.

The capsule shell of the second composition of matter aspect of the invention can be any pharmaceutically acceptable capsule shell but is preferably a gelatin capsule shell and can be a soft gelatin capsule shell or a hard gelatin capsule shell but is preferably a hard gelatin capsule shell and is of suitable size for containing from about 40 milligrams to about 700 milligrams of the first or second composition of matter aspect of the invention. Conventional machinery and technique are used in filling the capsule shells.

In the first process aspect of the invention the dissolution and suspension steps are carried out with conventional mixing equipment. Dissolution is preferably carried out with warming. The temperature of warming can be in the range from room temperature to about 100° C. and is preferably in the range from 50° C. to 60° C. Suspension of the drug in the aqueous hydroxypropyl methylcellulose or hydroxypropyl cellulose-plasticizer solution is carried out with vigorous agitation. In both process aspects of the invention the coating steps are preferably carried out using a fluid bed processor with inlet air temperature in the range from 50° C. to 70° C. with preheating of the sugar or sugar/starch beads whereby the water or ethanol-water is evaporated as the coating is applied. After drying the coated beads are sifted to produce coated beads of the desired particle size.

The first coating is from about 1% to about 500% by weight of the beads as stated above and is preferably from about 5% to about 50% by weight of the beads. The second coating is from about 3% to about 50% by weight of the beads as stated above and is preferably from about 3% to about 20% by weight of the beads. The additional first coating is from about 1% to about 100% by weight of the beads as stated above and is preferably from about 1% to about 10% by weight of the beads. The capsules are filled with from about 40 milligrams to about 700 milligrams of the coated beads as stated above and are preferably filled with from about 100 milligrams to about 500 milligrams of the coated beads.

The following compositions in accordance with the invention were prepared.

EXAMPLE

First-coated beads having the following composition were prepared.

| Ingredient | Percent by Weight |
|---|---|
| Milrinone (micronized) | 10.4 |
| Hydroxypropyl Methylcellulose 2910 USP (6 centipoises) | 2.09 |
| Triacetin USP | 0.416 |
| Sugar Spheres USP (20–25 mesh) | 87.1 |
| Total | 100.0 |

Second-coated beads having the following composition were then prepared from first-coated beads having the foregoing composition.

| Ingredient | Percent by Weight |
|---|---|
| Milrinone (micronized) | 9.56 |
| Hydroxypropyl Methylcellulose 2910 USP (6 centipoises) | 1.92 |
| Triacetin USP | 0.382 |
| Sugar Spheres USP (20–25 mesh) | 80.1 |
| Ethylcellulose NF (50 centipoises) | 3.27 |
| Ethylcellulose NF (10 centipoises) | 1.09 |
| Hydroxypropyl Cellulose NF | 1.67 |
| Polyvinyl Acetate Phthalate NF | 1.32 |
| Diacetylated Monoglycerides NF | 0.735 |
| Total | 100.0 |

Additional first coating was then added to second-coated beads having the foregoing composition. The resulting additionally coated beads having the following composition were then filled into size 3 white opaque hard gelatin capsules having an average weight of 54.0 mg affording filled capsules each having the following composition.

| Ingredient | Percent by Weight | Mg/Capsule |
|---|---|---|
| Milrinone (micronized) | 11.6 | 20.0 |
| Hydroxypropyl Methylcellulose 2910 USP (6 centipoises) | 2.33 | 4.02 |
| Triacetin USP | 0.464 | 0.800 |
| Sugar Spheres USP (20–25 mesh) | 77.8 | 134. |
| Ethylcellulose NF (50 centipoises) | 3.17 | 5.46 |
| Ethylcellulose NF (10 centipoises) | 1.06 | 1.83 |
| Hydroxypropyl Cellulose NF | 1.62 | 2.79 |
| Polyvinyl Acetate Phthalate NF | 1.28 | 2.21 |
| Diacetylated Monoglycerides NF | 0.714 | 1.23 |
| Total | 100.0 | 172. |

We claim:

1. Sugar or sugar/starch beads coated with from about 1% to about 500% by weight of the beads of a first coating consisting essentially of from about 10% to about 90% by weight of a drug having a solubility of at least 5% by weight in gastric fluid and less than 1% by weight in intestinal fluid, from about 10% to about 20% by weight of hydroxypropyl methylcellulose or hydroxypropyl cellulose and from about 1% to about 10% by weight of a plasticizer selected from the group consisting of triacetin, diacetylated monoglycerides, glycerin, propylene glycol, polyethylene glycol, diethyl phthalate and triethyl citrate or a mixture of two or more thereof and from about 3% to about 50% by weight of the beads of a second coating consisting essentially of from about 30% to about 50% by weight of ethylcellulose having a viscosity from 40 to 60 centipoises, from about 10% to about 30% by weight of ethylcellulose having a viscosity from 1 to 20 centipoises, from about 10% to about 30% by weight of hydroxypropyl cellulose, from about 10% to about 30% by weight of polyvinyl acetate phthalate and from about 1% to about 20% by weight of a plasticizer selected from diacetylated monoglycerides and triacetin or a mixture thereof.

2. Coated beads according to claim 1 additionally coated with from about 1% to about 100% by weight of the beads of the same first coating thereof.

3. Coated beads according to claim 1 having from about 5% to about 50% by weight of the beads of the first coating and from about 3% to about 20% by weight of the beads of the second coating.

4. Coated beads according to claim 3 additionally coated with from about 1% to about 10% by weight of the beads of the same first coating thereof.

5. The method of preparing coated beads according to claim 1 which comprises dissolving the hydroxypropyl methylcellulose or hydroxypropyl cellulose and the plasticizer selected from triacetin, diacetylated monoglycerides, glycerin, propylene glycol, polyethylene glycol, diethyl phthalate and triethyl citrate or mixture of two or more thereof in water with or without warming, suspending the drug in the resulting solution, coating the beads with the resulting first coating suspension, dissolving the 40–60 centipoise ethylcellulose, the 1–20 centipoise ethylcellulose, the hydroxypropyl cellulose, the polyvinyl acetate phthalate and the plasticizer selected from diacetylated monoglycerides and triacetin or mixture thereof in a mixture of ethanol and water with or without warming, and coating the first-coated beads with the resulting second coating solution.

6. The method according to claim 5 which comprises coating the coated beads thereof with additional first-coating suspension.

7. Sugar or sugar/starch beads coated with from about 1% to about 500% by weight of the beads of a first coating consisting essentially of from about 10% to about 90% by weight of a 1,2-dihydro-6-(lower alkyl)-2-oxo-5-(4-pyridinyl)-nicotinonitrile having a solubility of at least 5% by weight in gastric fluid and less than 1% by weight in intestinal fluid, from about 10% to about 20% by weight of hydroxypropyl methylcellulose and from about 1% to about 10% by weight of triacetin and from about 3% to about 50% by weight of the beads of a second coating consisting essentially of from about 30% to about 50% by weight of ethylcellulose having a viscosity from 40 to 60 centipoises, from about 10% to about 30% by weight of ethylcellulose having a viscosity from 1 to 20 centipoises, from about 10% to about 30% by weight of hydroxypropyl cellulose, from about 10% to about 30% by weight of polyvinyl acetate phthalate and from about 1% to about 20% by weight of diacetylated monoglycerides.

8. Coated beads according to claim 7 wherein the 1,2-dihydro-6-(lower alkyl)-2-oxo-5-(4-pyridinyl)-nicotinonitrile is 1,2-dihydro-6-methyl-2-oxo-5-(4-pyridinyl)-nicotinonitrile.

9. Coated beads according to claim 8 wherein the 1,2-dihydro-6-methyl-2-oxo-5-(4-pyridinyl)-nicotinonitrile is micronized.

10. Coated beads according to claim 9 having from about 5% to about 50% by weight of the beads of the first coating and from about 3% to about 50% by weight of the beads of the second coating.

11. Coated beads according to claim 10 additionally coated with from about 1% to about 100% by weight of the beads of the same first coating thereof.

12. Coated beads according to claim 11 additionally coated with from about 1% to about 10% by weight of the beads of the same first coating thereof 13. The method of preparing coated beads according to claim 12 which comprises dissolving the hydroxypropyl methylcellulose and triacetin in water with or without warming, suspending the 1,2-dihydro-6-methyl-2-oxo-5-(4-pyridinyl)-nicotinonitrile in the resulting solution, coating the beads with the resulting first coating suspension, dissolving the 40–60 centipoise ethylcellulose, the 1–20 centipoise ethylcellulose, the hydroxypropyl cellulose, the polyvinyl acetate phthalate and the diacetylated monoglycerides in a mixture of ethanol and water with or without warming, coating the first-coated beads with the resulting second coating solution, and coating the resulting coated beads with additional first-coating suspension.

* * * * *